United States Patent [19]

Ratcliffe

[11] 4,361,512
[45] Nov. 30, 1982

[54] 2-SUBSTITUTED THIO-6-SUBSTITUTED-CARBAPEN-2-EM-3-CARBOXYLIC ACIDS

[75] Inventor: Ronald W. Ratcliffe, Matawan, N.J.

[73] Assignee: Merck & Co., Inc., Rahway, N.J.

[21] Appl. No.: 210,691

[22] Filed: Nov. 26, 1980

[51] Int. Cl.³ .......................................... C07D 487/04
[52] U.S. Cl. ............................. 260/245.2 T; 424/274; 544/144; 546/272
[58] Field of Search .................. 260/245.2 T; 546/272; 544/144

[56] References Cited

U.S. PATENT DOCUMENTS

| 4,208,330 | 6/1980 | Christensen et al. | 260/245.2 T |
| 4,226,870 | 10/1980 | Christensen et al. | 260/245.2 T |
| 4,235,917 | 11/1980 | Christensen et al. | 260/245.2 T |
| 4,235,920 | 11/1980 | Christensen et al. | 260/245.2 T |

FOREIGN PATENT DOCUMENTS 1628  5/1979  European Pat. Off. ..... 260/245.2 T

Primary Examiner—Mary C. Lee
Attorney, Agent, or Firm—Hesna J. Pfeiffer; James A. Arno

[57] ABSTRACT

Disclosed are 2-substituted thio-6-substituted-carbapen-2-em-3-carboxylic acids (I) and their pharmaceutically acceptable salt, ester and amide derivatives which are useful as antibiotics:

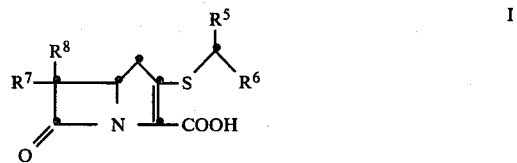

wherein:
$R^5$ is CN,

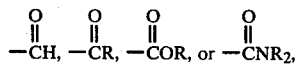

(R is alkyl or aryl);
$R^6$ is hydrogen, $R^5$, alkyl, aryl or heteroaryl; and
$R^7$ and $R^8$ are, inter alia, hydrogen, alkyl, alkenyl, aryl and aralkyl.

3 Claims, No Drawings

2-SUBSTITUTED THIO-6-SUBSTITUTED-CARBAPEN-2-EM-3-CARBOXYLIC ACIDS

BACKGROUND OF THE INVENTION

This invention relates to certain 2-substituted thio-6-substituted-carbapen-2-em-3-carboxylic acids (I) and their pharmaceutically acceptable salt, ester and amide derivatives which are useful as antibiotics:

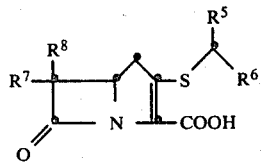

wherein:
$R^7$ and $R^8$ are independently selected from the group consisting of hydrogen, substituted and unsubstituted: alkyl having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl such as phenyl; aralkyl, wherein the aryl moiety is phenyl and the alkyl chain has 1-6 carbon atoms; heteroaryl, heteroaralkyl, heterocyclyl and heterocyclylalkyl wherein the substituent or substituents relative to the above-named radicals are selected from the group consisting of: amino, mono-, di- and trialkylamino, amido, hydroxyl, alkoxyl, acyloxy, sulfamoyl, ureido, amidino, guanidino, nitro, chloro, bromo, fluoro, cyano and carboxy; and wherein the hetero atom or atoms in the above-named heterocyclic moieties are selected from the group consisting of 1-4 oxygen or nitrogen atoms; and wherein the alkyl moieties of the above-recited substituents have 1-6 carbon atoms.

$R^5$ is, inter alia, cyano; substituted and unsubstituted: acyl such as

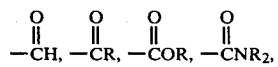

(R is substituted or unsubstituted: phenyl or alkyl having from 1-10 carbon atoms);

$R^6$ is, inter alia, hydrogen; $R^5$; substituted or unsubstituted: alkyl having from 1-10 carbon atoms; aryl, such as phenyl; and heteroaryl, such as furyl, but in general having from 4-6 atoms in the ring wherein the hetero atom or atoms are selected from oxygen, or nitrogen. Relative to the above definitions of $R^5$ and $R^6$ the substituent or substituents thereon may be selected from the group consisting of bromo, chloro, fluoro, nitro, cyano, alkoxycarbonyl having from 2-7 carbon atoms, alkoxyl having from 1-6 carbon atoms, phenyloxy, dialkylamino, and alkylarylamino wherein relative to the last two mentioned substituents the alkyl moiety has from 1-6 carbon atoms and the aryl moiety has from 1-6 carbon atoms and the aryl moiety is phenyl. The groups $R^7$, $R^8$, $R^5$ and $R^6$ are additionally defined below.

This invention also relates to the carboxyl derivatives of I which are antibiotics and which may be represented by the following generic structure (I):

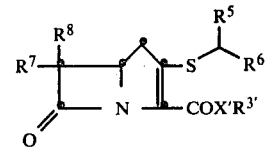

wherein X' is oxygen, sulphur or NR' (R'=H or lower alkyl having 1-6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in greater detail below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as S. aureus, Strep. pyogenes and B. subtilis, and gram negative bacteria such as E. coli, Pseudomonas, Proteus morganii, Serratia, and Klebsiella. Further objects of this invention are to provide chemical processes for the preparation of such antibiotics and their non-toxic pharmaceutically acceptable salts and esters; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention are prepared by a side chain interchange reaction involving starting material 1 and a diazo reagent 1a calculated to provide radicals $R^5$ and $R^6$:

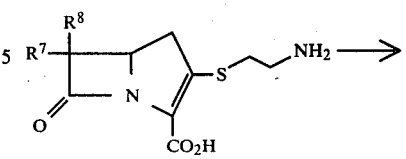

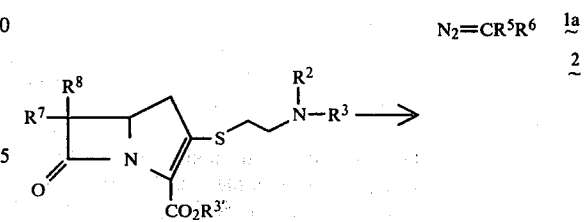

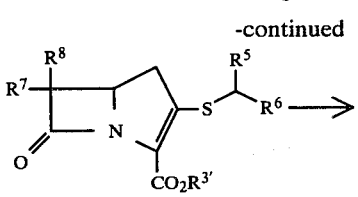

-continued

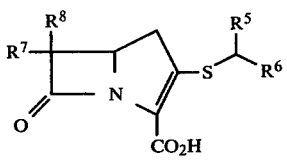

Starting material 1 are known. See for example, co-pending, commonly assigned U.S. Patent Applications Ser. Nos. 933,681 and 031,694 filed Aug. 17, 1978, now abandoned and Apr. 19, 1979, now abandoned respectively. To the extent that the above-cited pending U.S. applications disclose starting materials 1 and the values permissible for $R^7$ and $R^8$ they are hereby incorporated by reference. Also incorporated by reference are the following publications which disclose specific embodiments of starting material 1:
1. U.S. Pat. No. 3,950,357;
2. U.S. Pat. No. 4,234,596;
3. EPO Publication No. 0001628 Application No. 78101157.2.

In words relative to the above reaction scheme, starting material 1 is protected according to known procedures to obtain intermediate species 2. Typically, substituents $R^2$ and $R^3$ are selected from loweralkyl having from 1-6 carbon atoms, acyl such as acetyl or benzoyl, for example, or a triorganosilyl group such as trimethylsilyl. In the alternative, $R^2$ and $R^3$ may be joined together to form a blocked amino group such as phthalimido or succinimide. The carboxyl protecting group $R^{3'}$ is also established in this stage of the scheme. If $R^{3'}$ is not chosen as a pharmaceutically acceptable ester moiety, it is taken as a readily removable carboxyl protecting group such as benzyl, p-nitrobenzyl, p-methoxybenzyl, o-nitrobenzyl, 2-trimethylsilylethyl or a triorganosilyl group such as trimethylsilyl or the like. Intermediate species 2 are representatively prepared in the Examples which follow. However, it should be noted that preparation of such species (1→2) is fully demonstrated in the following co-pending, commonly assigned U.S. Patent Applications which are directed to certain O-, N- and carboxyl derivatives of thienamycin: U.S. Patent Applications Ser. Nos. 861,234 (filed Dec. 16, 1977), now U.S. Pat. No. 4,208,330; Ser. No. 861,235 (filed Dec. 16, 1977), now U.S. Pat. No. 4,235,920; Ser. No. 793,974 (filed May 5, 1977), now U.S. Pat. No. 4,235,917. These co-pending applications are directed to selected embodiments of intermediate species 2 having the structure:

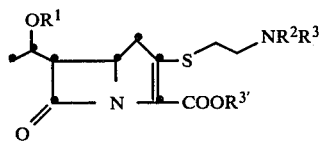

wherein $R^2$, $R^3$ and $R^{3'}$ are as defined above and $R^1$ is alkyl, acyl or a readily removable alcohol protecting group. Thus, to the extent that U.S. Pat. Nos. 4,226,870 and 4,235,920 provide a disclosure for the establishment for protecting groups $R^2$, $R^3$ and $R^{3'}$ (and the protection of any hydroxyl groups borne by substituents $R^7$ and $R^8$), they are hereby incorporated by reference since the protecting step in the above scheme 1→2 follows by analogy to the disclosed schemes.

In connection with the identity of the carboxyl substituent $R^{3'}$ it should be noted that when $R^{3'}$ is a conventionally known, bio-labile, pharmaceutically acceptable ester moiety, then the ultimate deblocking 3→I is not conducted. When, however, $R^{3'}$ is a conventional protecting group its removal is accomplished in the reaction 3→I and is discussed below.

The reaction 2→3 is accomplished by treating 2 in a solvent such as tetrahydrofuran, dimethoxyethane, toluene or the like with the diazo reagent 1a ($N_2=CR^5R^6$) of choice calculated to provide substituents $R^5$ and $R^6$ in the presence of a catalyst such as Cu, $CuSO_4$, Cu-bronze, CuCl, $Cu(acac)_2$, $Rh_2(OAc)_4$, $Pd(OAc)_2$ or the like. The reaction is conducted at a temperature of from 25° to 100° C. for from 0.5 to 5 hours to provide 3 [Relative to the above catalysts, "acac"=acetylacetanato or 2,4-pentanedionate; Ac=acetate.]

The reaction 3→I, the final deblocking of $R^{3'}$, is typically accomplished by treating 3 in a solvent such as dioxane, water, methanol or the like to a hydrogenation procedure. Typically this is accomplished under 1-4 atmospheres of hydrogen at a temperature of 10°-50° C. for from 0.5 to 4 hours in the presence of a hydrogenation catalyst such as palladium on charcoal, palladium hydroxide, or platinum oxide.

Relative to the generic representation of the compounds of the present invention, I, the most preferred values for $R^5$ include:
CHO
—COϕ (ϕ=phenyl)
—$CO_2Et$ (Et=ethyl)
—$CO_2CH_2$ϕ

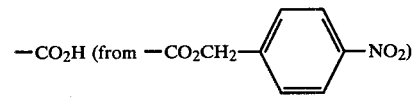

—$CON(CH_3)_2$
—$COCH_3$
—CN.

The most preferred values for $R^6$ include: H, $CH_3$, phenyl, —$CO_2Et$:

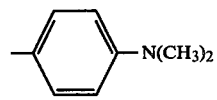

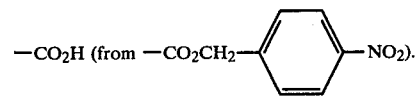

A representative list of the diazo reagents bearing radicals $R^5$ and $R^6$ is as follows:

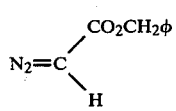

-continued

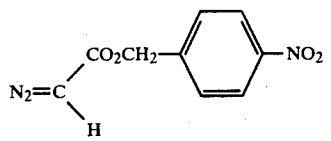

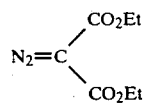

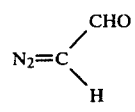

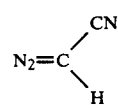

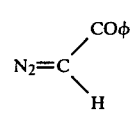

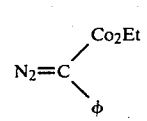

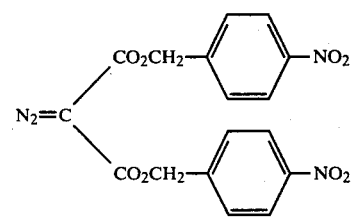

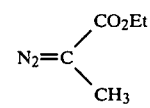

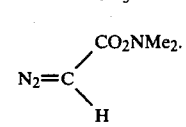

A particularly preferred set of values for $R^7$ and $R^8$ is when one is hydrogen and the other is 1-hydroxyethyl or O-derivatives thereof:

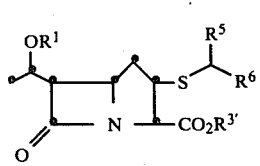

wherein $R^{3'}$, $R^5$ and $R^6$ are as defined above and $R^1$ is hydrogen, alkyl having 1-6 carbon atoms or acyl such as acetyl, sulfo or the like.

As noted above, the compounds of the present invention may also generally be represented by the following structural formula:

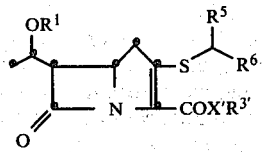

wherein X' is oxygen, sulfur or NR' (R' is hydrogen or loweralkyl having from 1 to 6 carbon atoms); and $R^{3'}$ is hydrogen, or, inter alia, is representatively selected to provide the pharmaceutically acceptable salt, ester anhydride ($R^{3'}$ is acyl) and amide moieties known in the bicyclic β-lactam antibiotic art. Identification of the Radical —COX'R$^{3'}$ In the generic representation of the compounds of the present invention (I, above), the radical represented by —COX'R$^{3'}$ is, inter alia, —COOH (X' is oxygen and $R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and the nuclear analogues thereof.

Suitable radicals ($R^{3'}$ include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable derivatives of the present invention falling in this class are given below. Suitable blocking esters thus include those selected from the following list which is representative and not intended to be an exhaustive list of possible ester groups, wherein X'=O and $R^{3'}$ is given:

(i) $R^{3'}=CR^aR^bR^c$ wherein at least one of $R^a$, $R^b$ and $R^c$ is an electron-donor, e.g., p-methoxyphenyl. The remaining $R^a$, $R^b$ and $R^c$ groups may be hydrogen or organic substituting groups. Suitable ester groups of this type include p-methoxybenzyloyxcarbonyl.

(ii) $R^{3'}=CR^aR^bR^c$ wherein at least one of $R^a$, $R^b$ and $R^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^{3'}=CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula: $R^4{}_3SiX'$ wherein X' is a halogen such as chloro or bromo and $R^4$ is alkyl, e.g., methyl, ethyl, t-butyl.

More generally stated, pharmaceutically acceptable carboxyl derivatives of the present invention are those derived by reacting I with alcohols, acylating reagents and the like. For example, esters and amides of interest are the above-listed starting materials and final products having the —COX'R$^{3'}$ group at the 3-position; wherein X' is oxygen, sulfur or NR' (R' is H or R$^{3'}$), and $R^{3'}$ is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkyl portion has 1-6 carbon atoms, such as pivaloyloxymethyl;

haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, and 4-butenyl; aralkyl and lower alkoxyl- and nitro- substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

group. Representative of such amides are those wherein R' is selected from the group consisting of hydrogen and lower alkyl such as methyl and ethyl.

The most preferred —COX'R$^{3'}$ radicals of the present invention are those wherein (relative to Structure I above), X is oxygen and R$^{3'}$ is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The products of this invention (I) form a wide variety of pharmacologically acceptable salts with inorganic and organic bases; these include, for example, metal salts derived from alkali or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N-dibenzylethylenediamine, diethanolamine, piperazine, dimethylaminoethanol, 2-amino-2-methyl-1-propanol, theophylline, N-methylglucamine and the like.

The salts can be mono salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The compounds of the present invention are valuable antimicrobial substances which are active against various gram-positive and gram-negative pathogens. Thus, the free acid, and especially the salts thereof such as amine and metal salts, particularly the alkali metal and alkaline earth metal salts, are useful bactericides and can be used for removing susceptible pathogens from dental and medical equipment for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram positive or gram-negative bacteria, for example against *Staphylococcus aureus*, *Escherichia coli*, *Klebsiella pneumoniae*, *Bacillus subtilis*, *Salmonella typhosa*, Pseudomonas and *Bacterium proteus*. The antibacterials of the invention may further be utilized as additives to animal feeding-stuffs, for preserving foodstuffs and disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in only or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, or throat paints. For medication of the eyes or ears, the preparations may be presented as individual capsules, in liquid or semi-solid form, or may be used as drops. Topical applications may be formulated in hydrophobic or hydrophilic bases as ointments, creams, lotions, paints, or powders.

Also, in addition to a carrier, the instant compositions may include other ingredients such as stabilizers, binders, antioxidants, preservatives, lubricants, suspending agents, viscosity agents or flavoring agents. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated, her weight, and the route and frequency of administration. The parenteral route, by injection, being preferred for generalized infections, and the oral route for intestinal infections. In general, a daily oral dosage consists of from about 5 to about 600 mg. of active ingredient per kg. of body weight of the subject in one or more applications per day. A preferred daily dosage for adult humans lies in the range of from about 15 to 240 mg. of active ingredient per kg. of body weight.

The instant compositions may be administered in several unit dosage forms as, for example, in solid or liquid orally ingestible dosage form. The compositions per unit dosage, whether liquid or solid, may contain from 0.1% to 99% of active material; the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention. All reaction temperatures are in °C.

EXAMPLE 1

Sodium 2-(2-phthalimido)ethylthio-6-(1-hydroxy)ethylcarbapen-2-em-3-carboxylate

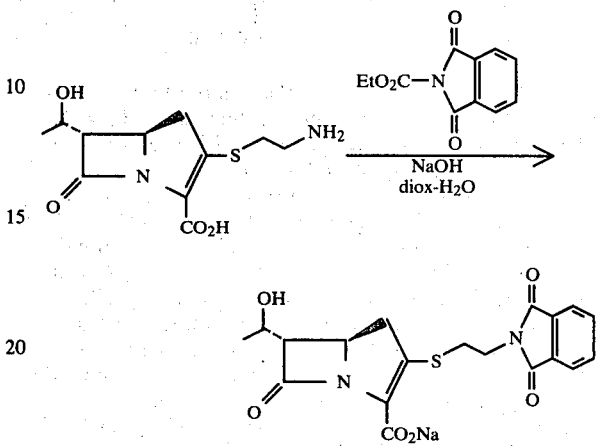

A solution of thienamycin (0.79 g, 91% pure by UV, 2.64 mmol) in ice-cold 0.1 M pH 7 phosphate buffer (30 ml) is brought to pH 8.5 by addition of 1 N sodium hydroxide (1.0 ml) and then treated dropwise over ca. one minute with a solution of N-carbethoxyphthalimide (1.16 g, 5.3 mmol) in dioxane (6 ml). A precipitate appears immediately. The resulting mixture is stirred with ice-bath cooling and the pH is maintained at 8.5 by periodic addition of 1 N sodium hydroxide solution (2.7 ml over 1 hour). After 1 hour, the mixture is acidified to pH 7 with ice-cold 2.5 N hydrochloric acid and extracted with cold ethyl acetate (2×30 ml). The aqueous portion is cooled in an ice-bath, layered with cold ethyl acetate (30 ml), stirred, and acidified to pH 3 with 2.5 N hydrochloric acid. The layers are separated and the aqueous portion is extracted with more ethyl acetate (2×10 ml). The combined ethyl acetate solution is washed with cold brine, then layered with ice-cold water (30 ml), stirred in an ice-bath, and slowly brought to pH 7 by addition of cold aqueous 5% sodium bicarbonate solution. The aqueous portion is separated, spun on a rotary evaporator to remove dissolved ethyl acetate, and lyophilized to provide the title compound (1.03 g) as a pale yellow, amorphous solid: UV (H$_2$O)300 nm; IR (nujol) 1760, 1700, 1680 and 1610 cm$^{-1}$; NMR (D$_2$O) δ1.23(d, 3, J=6.5, CH$_3$), 3.09 (m, 2, SCH$_2$), 3.24 (m 2, CH$_2$), 3.28 (dd, 1, J=2.5 and 6.5, H6), 4.17 (dq, 1, J=6.5 and 6.5, C$\underline{H}$CH$_3$), 4.25 (m, 1, H5), and 7.88 (m, 4, C$_6$H$_4$).

EXAMPLE 2 p-Nitrobenzyl 2-(2-phthalimido)ethylthio-6-(1-hydroxy)ethyl-carbapen-2-em-3-carboxylate

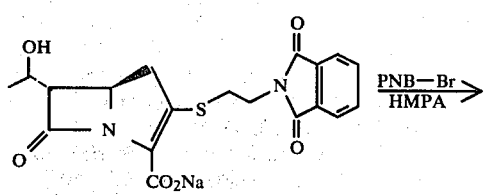

-continued

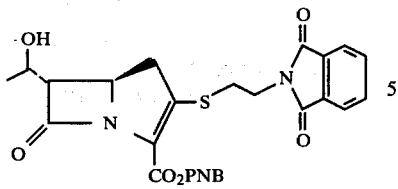

A mixture of sodium 2-(2-phthalimido)ethylthio-6-(1-hydroxy)ethyl-carbapen-2-em-3-carboxylate (1.03 g, 2.4 mmol) and p-nitrobenzyl bromide (1.08 g, 5 mmol) in anhydrous hexamethylphosphoramide (10 ml) is stirred under a nitrogen atmosphere at room temperature for 4 hours. The mixture is diluted with ethyl acetate (100 ml), washed with water (5×20 ml) and brine, dried with magnesium sulfate, and concentrated in vacuo to ca. 10 ml volume. The resulting suspension is slowly diluted with diethyl ether (25 ml) and then filtered to remove the precipitate. This material is washed with diethyl ether and dried in vacuo to provide the title compound (0.84 g, 59% yield from thienamycin) as an off-white, fibrous solid: mp 144°–146°; IR(CH$_2$Cl$_2$) 1780 and 1721 cm$^{-1}$; NMR (CDCl$_3$) δ1.38 (d, 3, J=6.2, CHC$\underline{H}$$_3$), 3.12 (m, 2, SCH$_2$), 3.24 (dd, 1, J=8.5 and 18.2, H1a), 3.28 (dd, 1, J=3 and 6.5, H6), 3.53 (dd, 1, J=9.8 and 18.2, H1b), 3.92 (m, 2, NCH$_2$), 4.29(m, 2, H5 and CHC$\underline{H}$$_3$), 5.26 and 5.51 (two d's, 2, J=14, CH$_2$Ar), 7.68 and 8.25 (two d's, 4, J=8, p-NO$_2$C$_6$H$_4$), 7.80 and 7.90 (two m's, 4, C$_6$H$_4$).

EXAMPLE 3
p-Nitrobenzyl 2-(2-phthalimido)ethylthio-6-(1-acetoxy)ethyl-carbapen-2-em-3-carboxylate

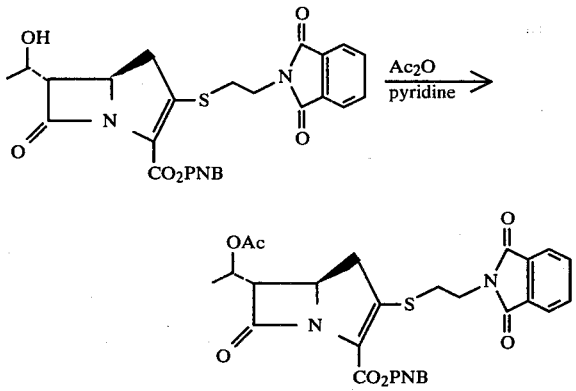

A solution of p-nitrobenzyl 2-(2-phthalimido) ethylthio-6-(1-hydroxy)ethyl-carbapen-2-em-3-carboxylate (108 mg, 0.2 mmol) in anhydrous pyridine (1 ml) is cooled in an ice-bath and stirred. Some of the starting material precipitates out. The mixture is treated with acetic anhydride (0.19 ml, 2 mmol) and the resulting suspension is stirred overnight (17 hours) in the cold. The resulting solution is slowly diluted with diethyl ether (20 ml) to give a precipitate which is aged in the cold. The precipitate is collected, washed with diethyl ether, and dried in vacuo to provide the title compound (102 mg) as a cream colored powder: IR(CH$_2$Cl$_2$) 1778 and 1717 cm$^{-1}$; NMR (CDCl$_3$) δ1.41(d, 3, J=6.7, CHC$\underline{H}$$_3$), 2.09 (s, 3, COCH$_3$), 3.11 (m, 2, SCH$_2$), 3.22 (dd, 1, J=8.6 and 18, H1a), 3.39(dd, 1, J=2.6 and 7.2, H6), 3.49(dd, 1, J=9.8 and 18, H1b), 3.91(m, 2, NCH$_2$), 4.23 (apparent dt, 1, J=2.6 and 9.2, H5), 5.26 and 5.48 (two d's, 2, J=14, CH$_2$Ar), 5.28 (m, 1, CHC$\underline{H}$$_3$), 7.66 and 8.25 (two d's, 4, J=8, p-NO$_2$C$_6$H$_4$), 7.78 and 7.89 (two m's, C$_6$H$_4$).

EXAMPLE 4
p-Nitrobenzyl 2-benzyloxycarbonylmethylthio-6-(1-acetoxy)ethyl-carba-pen-2-em-3-carboxylate

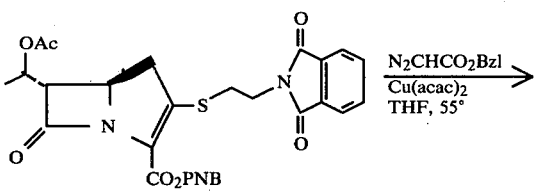

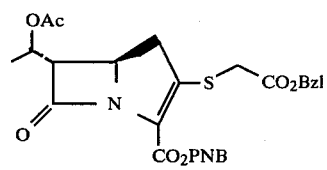

A solution of p-nitrobenzyl 2-(2-phthalimido)ethylthio-6-(1-acetoxy)ethyl-carbapen-2-em-3-carboxylate (101 mg, 0.174 mmol) and copper (II) 2,4-pentanedionate (4.5 mg, 0.017 mmol) in anhydrous tetrahydrofuran (3 ml) is stirred under a nitrogen atmosphere and heated in an oil bath maintained at 55°–57°. A solution of benzyl diazoacetate (307 mg, 1.74 mmol) in anhydrous tetrahydrofuran (0.5 ml) is then added dropwise over 27 minutes. Gas evolution is noticed ca. 15 minutes after beginning the diazoacetate addition and gas evolution ceases ca. 15 minutes following the addition, at which time the mixture is a clear amber solution. The mixture is heated 60 minutes following the addition, then diluted with ethylacetate (30 ml), washed with water (4×10 ml) and brine, dried with magnesium sulfate, filtered, and evaporated under vacuum to an amber oil (368 mg). This material is chromatographed on two 1 mm×20×40 cm silica gel GF plates using 9:1 toluene-ethylacetate as developing solvent. The UV visible band at R$_f$0.18 is removed and eluted with ethyl acetate to provide the title compound (21 mg) as an oil: IR(CH$_2$Cl$_2$) 1777, 1730, 1522, and 1348 cm$^{-1}$; NMR (CDCl$_3$) δ1.38 (d, 3, J=7, CH$_3$), 2.08(s, 3, COCH$_3$), 3.03(dd, 1, J=8.5 and 18, H1a), 3.23(dd, 1, J=2.7 and 8, H6), 3.30(dd, 1, J=10 and 18, H1b), 3.58(ABq, 2, J=15, CH$_2$CO$_2$Bzl), 4.10 (~dt, 1, J=2.5 and 9, H5), 5.21 (m, 1, C$\underline{H}$CH$_3$), 5.20(s, 2, CH$_2$φ), 5.28 and 5.52 (two d's, 2, J=14, CH$_2$Ar), 7.39 (s, 5, C$_6$H$_5$), 7.68 and 8.26 (two d's, 4, J=9, C$_6$H$_4$); mass spectrum m/e 554 (M), 512 (M—CH$_2$CO), 510 (M—CO$_2$), 494(M-HOAc), 468, 426, 136, and 91; UV (dioxane) 271 and 316 nm.

PREPARATION OF BENZYL DIAZOACETATE

A mixture of benzyl glycinate p-toleuensulfonic acid salt (674 mg), sodium nitrite (690 mg), methylene chloride (40 ml) and water (20 ml) is treated with p-toluenesulfonic acid monohydrate (380 mg) and shaken vigorously for 5 minutes. The methylene chloride layer is separated, washed with aqueous 5% sodium bicarbonate (2×20 ml) and brine, dried with magnesium sulfate, filtered, and evaporated under vaucum to give the diazoacetate (322 mg) as a yellow liquid.

EXAMPLE 5

Sodium 2-benzyloxycarbonylmethylthio-6-(1-acetoxy)ethyl-carbapen-2-em-3-carboxylate

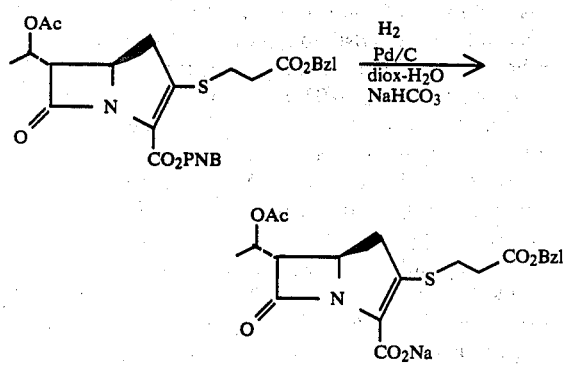

A solution of p-nitrobenzyl 2-benzyloxycarbonylmethylthio-6-(1-acetoxy)ethyl-carbapen-2-em-3-carboxylate (5.6 mg, 0.01 mmol) in dioxane (0.60 ml) is diluted with ethanol (0.05 ml) and water (0.35 ml) containing sodium bicarbonate (1.0 mg, 0.012 mmol). The solution is treated with 10% palladium on charcoal (5.5 mg) and hydrogenated at 40 psi for 30 minutes. The mixture is diluted with water (3 ml) and centrifuged to remove the catalyst which is washed with more water (2×1 ml). The combined aqueous supernatant is washed with ethyl acetate (4×2 ml), filtered through a cotton plug, concentrated in vacuo to ca. 1 ml, and lyophilized to yield the title compound as an amorphous solid: UV (0.1 M pH 7 phosphate buffer) 299 nm; NMR (D$_2$O) δ1.30 (d, 3, J=6.7, CH$_3$), 2.13 (s, 3, COCH$_3$), 2.81 (dd, 1, J=9 and 18, H1a), 3.05 (dd, 1, J=10 and 18, H1b), 3.31 (dd, 1, J=3 and 5, H6), ~3.7(m, SCH$_2$, obscured by impurities), 4.07 (m, 1, H5), 5.21 (m, 1, CHCH$_3$), 5.27(s, 2, CH$_2$φ) and 7.48 (s, 5, C$_6$H$_5$); electrophoresis in 0.05 M pH 6.9 buffer at 2 KV for 20 minutes gives a single bioactive zone moving 3–5 cm toward the anode; HPLC on a C$_{18}$ Bondapak Reverse phase column using 10% THF/H$_2$O at 1.0 ml/min gives a UV visible peak at retention time 17.4 mins (4.8 mins for thienamycin).

EXAMPLE 6 p-Nitrobenzyl 2-(2-phthalimido)ethylthio-6-(1-trimethylsilyloxy)ethyl-carbapen-2-em-3-carboxylate

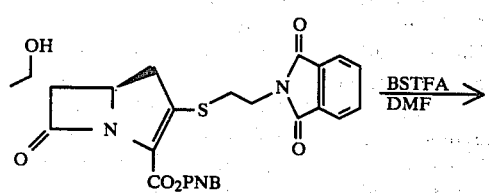

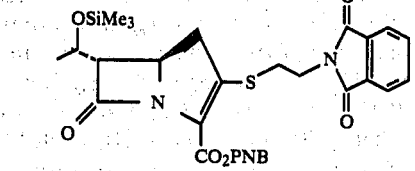

A solution of p-nitrobenzyl 2-(2-phthalimido)ethylthio-6-(1-hydroxy) ethyl-carbapen-2-em-3-carboxylate (269 mg, 0.5 mmol) in anhydrous dimethylformamide (2 ml) is treated with N,O-bis(trimethylsilyl)trifluoroacetamide (0.5 ml), and the resulting solution is kept at room temperature and under a nitrogen atmosphere for 2 hours. The solution is diluted with ethyl acetate (20 ml), washed with water (5×10 ml) and brine, dried with magnesium sulfate, filtered, and evaporated in vacuo to yield the title compound (232 mg) as an off-white powder: mp 134°–137°; IR (neat) 1774 and 1715 cm$^{-1}$; NMR (CDCl$_3$) δ0.14(s, 9, Si(CH$_3$)$_3$), 1.28 (d, 3, J=6, CHCH$_3$), 3.2 (m, 5, SCH$_2$, CH$_2$, and H$_6$), 3.93 (m, 2, NCH$_2$), 4.24(m,2, H5 and CHCH$_3$), 5.24 and 5.50 (two d's, 2, J=14, CH$_2$Ar), 7.68 and 8.24 (two d's J=9, p-NO$_2$C$_6$H$_4$), and 7.84 (m, 4, C$_6$H$_4$); mass spectrum m/e 609 (M), 594, 463, 451.

EXAMPLE 7 p-Nitrobenzyl 2-benzyloxycarbonylmethylthio-6-(1-hydroxy)ethyl-carbapen-2-em-3-carboxylate

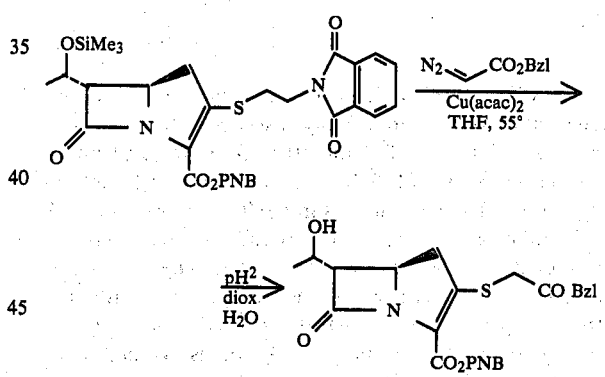

A solution of p-nitrobenzyl 2-(2-phthalimido) ethylthio-6-(1-trimethylsilyloxy)ethyl-carbapen-2-em-3-carboxylate (121.9 mg, 0.2 mmol) and copper (II) 2,4-pentanedionate (5.2 mg, 0.02 mmol) in anhydrous tetrahydrofuran (3 ml) is placed under a nitrogen atmosphere and heated with stirring in an oil bath maintained at 55°–57°. A solution of benzyl diazoacetate (352 mg, 2 mmol) in tetrahydrofuran (1 ml) is then added dropwise over 30 minutes. After stirring 60 more minutes at 55°–57°, the mixture is diluted with ethyl acetate (30 ml), washed with water (4×10 ml) and brine, dried with magnesium sulfate, filtered, and evaporated under vacuum to an amber oil (430 mg). This material is dissolved in dioxane (2 ml) and treated with 1 M pH 2 phosphate buffer (0.4 ml). The resulting mixture is stirred at room temperature for 90 minutes, then diluted with ethyl acetate (30 ml), washed with water (4×10 ml), aqueous 5% sodium bicarbonate (10 ml), and brine, dried with magnesium sulfate, filtered, and evaporated under vacuum to a yellow oil (396 mg).

Chromatography of this material on four 1.0 mm×20×20 cm silica gel GF plates using 1:1 toluene-ethyl acetate as developing solvent provides a UV visible band at R$_f$0.38 which is eluted with ethyl acetate to provide the title compound (8 mg) as an oil: IR(CH$_2$Cl$_2$) 3600, 1778, 1737, 1719, 1524, and 1348 cm$^{-1}$; NMR (CDCl$_3$) δ1.34 (d, 3, J=6, CH$_3$), 3.04 (dd, 1, J=8.5 and 18, H1a), 3.12 (dd, 1, J=2.7 and 6.6, H6), 3.30 (dd, 1, J=10 and 18, H1b), 3.59 (ABq, 2, J=15, CH$_2$CO$_2$Bzl), 4.17 (~dt, 1, J=2.7 and 9, H5), 4.23(m, 1,CHCH$_3$), 5.20 (s, 2, CH$_2$ϕ), 5.26 and 5.52 (two d's, 2, J=14, CH$_2$Ar), 7.38(m, 5, C$_6$H$_5$), 7.68 and 8.24 (two d's, 4, J=9, C$_6$H$_4$); UV (dioxane) 270 and 315 nm.

EXAMPLE 8

Sodium 2-benzyloxycarbonylmethylthio-6-(1-hydroxy)ethyl-carbapen-2-em-3-carboxylate

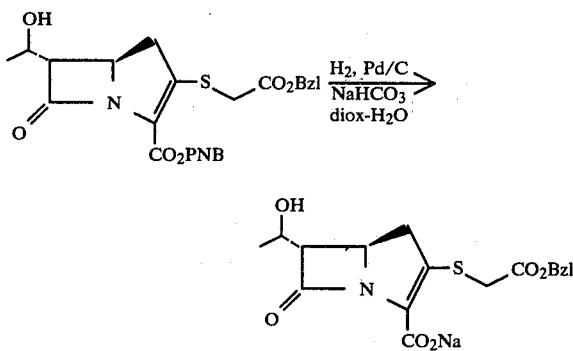

A solution of p-nitrobenzyl 2-benzyloxycarbonyl-methylthio-6-(1-hydroxy)ethyl-carbapen-2-em-3-carboxylate (7.1 mg, 0.014 mmol) in dioxane (0.84 ml) is treated with ethanol (0.07 ml), water (0.49 ml) containing sodium bicarbonate (1.4 mg, 0.017 mmol), and 10% palladium on charcoal (7.1 mg) and the mixture is hydrogenated at 40 psi for 30 minutes. The mixture is diluted to 3 ml with water and centrifuged to remove the catalyst which is washed with more water (2×1 ml). The combined aqueous solution is washed with ethylacetate (4×2 ml), filtered through a cotton plug, concentrated in vacuo to ca. 1 ml, and lyophilized to provide the title compound as a powder: UV (0.1 M pH 7 phosphate buffer) 300 nm; electrophoresis (0.05 M pH 7 phosphate buffer, 2 KV, 25 ma, 20 mins) gives a single bioactive zone migrating 3.5 cm toward the anode.

EXAMPLE 9 p-Nitrobenzyl 2-(p-nitrobenzyloxycarbonyl)methylthio-6-(1-hydroxy)ethyl-carbapen-2-em-3-carboxylate

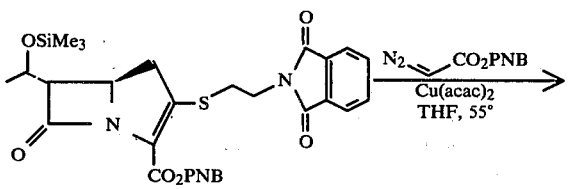

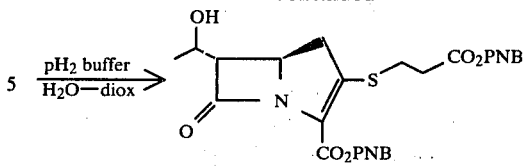

A solution of p-nitrobenzyl 2-(2-phthalimido)eth-ylthio-6-(1-trimethylsilyloxy)ethyl-carbapen-2-em-3-carboxylate (122 mg, 0.2 mmol) and copper (II) 2,4-pentanedionate (5.2 mg, 0.02 mmol) in anhydrous tetrahydrofuran (3 ml) is stirred under anitrogen atmosphere and heated in an oil bath at 54°-56° while a solution of p-nitrobenzyl diazoacetate (885 mg, 4 mmol) in tetrahydrofuran (2 ml) is added dropwise over 27 minutes. Gas evolution begins ca. 20 minutes after the start of the diazoacetate addition and ceases ca. 15 minutes after completion of the addition. The mixture is stirred and heated for 60 minutes following the addition, then diluted with ethyl acetate (30 ml), washed with water (4×10 ml) and brine, dried with magnesium sulfate, filtered and evaporated under vacuum to a yellow semi-solid (937 mg). This metal is suspended in dioxane (4 ml), treated with 1 M pH 2 phosphate buffer (1 ml), and stirred at room temperature for 90 minutes. The resulting mixture is diluted with ethylacetate (50 ml), washed with water (3×20 ml) and brine, dried with magnesium sulfate, filtered and evaporated in vacuo to a yellow semi-solid (854 mg). This material is taken up in methylene chloride (3 ml) and filtered to remove an off-white solid which was identified as a mixture of p-nitrobenzyl fumarate and maleate. The filtrate is streaked on two 1.0 mm×20×40 cm silica gel GF plates which are developed with 1:1 toluene-ethyl acetate. The UV visible band at R$_f$0.21 is removed and eluted with ethyl acetate to give an oil (16 mg) which consists of a mixture of the title compound and some p-nitrobenzyl 2-(2-phthalimido)ethylthio-6-(1-hydroxy)ethyl-carbapen-2-em-3-carboxylate: IR(CH$_2$Cl$_2$) 3570, 1775, 1737, 1710, 1522, and 1347 cm$^{-1}$; NMR (CDCl$_3$) δ 1.36 (d, 3, J=6, CH$_3$), 3.12 (dd, 1, J=8.5 and 17.7, H1a), 3.18 (dd, 1, J=2.4 and 7.5, H6), 3.38 (dd, 1, J=9.8 and 17.7, H1b), 3.63 (ABq, 2, J=15, SCH$_2$), 4.24 (m, 2, H5 and CHCH$_3$), 5.27 and 5.54 (two d's, 2, J=14, CH$_2$Ar), 5.29 (s, 2, SCH$_2$CO$_2$CH$_2$Ar) 7.54, 7.70, 8.26, and 8.27 (four d's, 8, J=9, two C$_6$H$_4$).

Preparation of p-nitrobenzyl diazoacetate

A mixture of p-nitrobenzyl glycinate hydrobromide (2.91 g, 10 mmol), water (100 ml), methylene chloride (200 ml), sodium nitrite (3.45 g, 50 mmol) and p-toluenesulfonic acid monohydrate (1.90 g, 10 mmol) is shaken vigorously for 5 minutes. The methylene chloride layer is separated, washed with aqueous 5% sodium bicarbonate (2×50 ml) and brine, dried with magnesium sulfate, filtered, and evaporated under vacuum to a yellow semi-solid (2.11 g). This material is chromatographed on a silica gel column (60 g) using 20:1 toluene-ethyl acetate as eluting solvent to afford the diazoacetate (1.57 g) as a yellow solid: IR(CH$_2$Cl$_2$) 2120, 1690, 1520, and 1345 cm$^{-1}$; NMR (CDCl$_3$) 4.90 (s, 1, CH), 5.30 (2, CH$_2$Ar) 7.53 and 8.23 (two d's, 4, J=8.5, C$_6$H$_4$).

EXAMPLE 10

Disodium 2-carboxymethylthio-6-(1-hydroxy)ethyl-carbapen-2-em-3-carboxylate

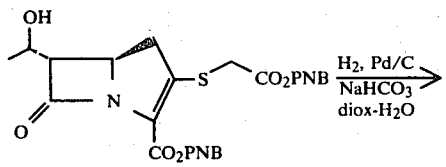

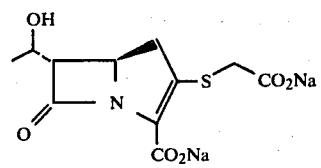

A solution of crude p-nitrobenzyl 2-(p-nitrobenzyloxycarbonyl)methylthio-6-(1-hydroxy)ethyl-carbapen-2-em-3-carboxylate (8.7 mg) in dioxane (1.20 ml) is diluted with ethanol (0.10 ml) and water (0.70 ml) containing sodium bicarbonate (2.3 mg). The resulting solution is treated with 10% palladium on charcoal (15 mg) and hydrogenated at 40 psi for 60 minutes. The mixture is diluted with water to 5 ml and centrifuged to remove the catalyst which is washed with more water (2×1 ml). The combined aqueous solution is washed with ethyl acetate (4×3 ml), filtered through a cotton plug, concentrated in vacuo to ca. 1 ml, and lyophilized to provide the title compound as a solid: UV (pH 7 phosphate buffer) 301 nm; electrophoresis (0.05 M pH 7 phosphate buffer 2 KV, 20 ma, 20 mins) gives a biactive zone migrating 9.3 cm toward the anode (dicarboxylate).

EXAMPLE 11

Following the foregoing text and Examples, the following compounds of the present invention are obtained in a precisely analogous manner when the indicated substitution is made.

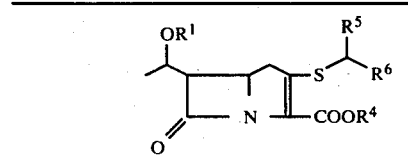

| COMPOUND | | | |
|---|---|---|---|
| $R^5$ | $R^6$ | $R^1$ | $R^4$ |
| $CO_2Et$ | H | H | Na |
| $CO_2Et$ | H | H | pivaloyloxymethyl |
| $CO_2Et$ | H | H | phthalidyl |
| $CO_2Et$ | H | Me | Na |
| $CO_2CH_2\phi$ | H | Me | Na |
| $CO\phi$ | H | H | Na |
| $CONMe_2$ | H | H | Na |
| $CO_2Et$ | $CO_2Et$ | H | Na |
| $CO_2Et$ | $CO_2Et$ | Ac | Na |
| $CO_2Et$ | $CO_2Et$ | Me | Na |
| $CO_2Et$ | $CO_2Et$ | H | pivaloyloxymethyl |
| $CO_2Na$ | $CO_2Na$ | H | Na |
| $CO_2Et$ | Me | H | Na |
| $CO_2Et$ | CHO | H | Na |
| $CO_2Et$ | CN | H | Na |

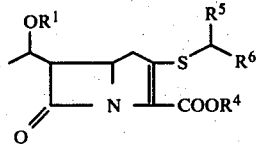

| COMPOUND | | | |
|---|---|---|---|
| $R^5$ | $R^6$ | $R^1$ | $R^4$ |
| $CO_2Et$ | -⌬-$NMe_2$ | H | H |
| $CO_2Et$ | $\phi$ | H | Na |
| $CO_2CH_2\phi$ | $\phi$ | H | Na |
| $CO\phi$ | CHO | H | Na |
| $CO\phi$ | $\phi$ | H | Na |
| $COCH_3$ | $\phi$ | H | Na |
| CHO | $\phi$ | H | Na |
| CHO | $\phi$ | Me | Na |
| CHO | $\phi$ | Ac | Na |
| CHO | $\phi$ | H | phthalidyl |
| $CO_2CH_2\phi$ | H | H | pivaloyloxymethyl |
| $CO_2CH_2\phi$ | H | H | phthalidyl |
| CN | $\phi$ | H | Na |
| CN | CN | H | Na |
| $CONMe_2$ | $CONMe_2$ | H | Na |

In the table, Et = ethyl; $\phi$ = phenyl; and Me = methyl.

EXAMPLE 12

Preparation of Pharmaceutical Compositions

One such unit dosage form is prepared by mixing 120 mg of sodium 2-benzyloxycarbonylmethylthio-6(1-hydroxy)ethyl-carbapen-2-em-3-carboxylate with 20 mg of lactose and 5 mg of magnesium stearate and placing the 145 mg. mixture into a No. 3 gelatin capsule. Similarly, by employing more of the active ingredient and less lactose, other dosage forms can be put in No. 3 gelatin capsules and should it be necessary to mix more than 145 mg. of ingredients together larger capsules such as compressed tablets and pills can also be prepared. The following examples are illustrative of the preparation of pharmaceutical formulations:

| TABLET | PER TABLET |
|---|---|
| sodium 2-benzyloxycarbonylmethyl-thio-6-(1-hydroxy)ethyl-carbapen-2-em-3-carboxylate | 125 mg. |
| Dicalcium Phosphate | 192 mg. |
| Cornstarch, U.S.P. | 6 mg. |
| Lactose, U.S.P. | 190 mg. |
| Magnesium Stearate | Balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| Sodium 2-benzyloxycarbonylmethyl-thio-6-(1-hydroxy)ethyl-carbapen-2-em-3-carboxylate | 500 mg. |
| Diluent: Sterile Water for Injection | 5 cc |

-continued

| OPTHALMIC SOLUTION | |
|---|---|
| Sodium 2-benzyloxycarbonylmethyl-thio-6-(1-hydroxy)ethyl-carbapen-2-em-3-carboxylate | 100 mg. |
| Hydroxypropylmethyl cellulose | 5 mg. |
| Sterile water | to 1 ml. |
| OTIC SOLUTION | |
| Sodium 2-benzyloxycarbonylmethyl-thio-6-(1-hydroxy)ethyl-carbapen-2-em-3-carboxylate | 100 mg. |
| Benzalkonium chloride | 0.1 mg. |
| Sterile water | to 1 ml. |
| TOPICAL OINTMENT | |
| Sodium 2-benzyloxycarbonylmethyl-thio-6-(1-hydroxy)ethyl-carbapen-2-em-3-carboxylate | 100 mg. |
| Polyethylene Glycol 4000 U.S.P. | 400 mg. |
| Polyethylene Glycol 400 U.S.P. | 1.0 gram. |

What is claimed is:

1. The process for preparing the compound of the formula:

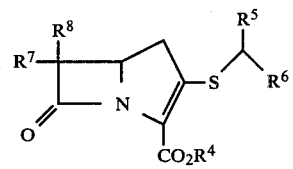  I which comprises reacting the compound of the formula:

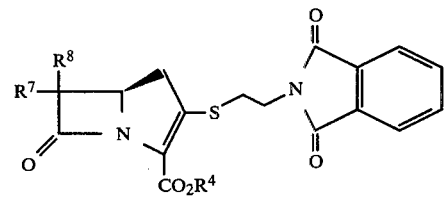  II with a diazo reagent:

  III wherein the reaction takes place by dissolving compound II in a solvent such as tetrahydrofuran, dimethoxyethane, or toluene; in the presence of a catalytic amount of a copper catalyst which is copper II 2,4-pentanedione; then adding an excess of the diazo reagent III; at a temperature of about 55°–57° C. for about 1.5 hours; then quenching and isolating the resultant product Compound I;

wherein $R^4$ is p-nitrobenzyl, p-methoxybenzyl, o-nitrobenzyl, 2-trimethylsilyl or trimethylsilyl, or benzyl;

$R^6$ is hydrogen, $CO_2CH_2CH_3$, $CH_3$, CHO, CN;

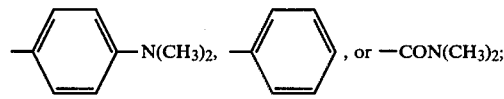

$R^5$ is $CO_2CH_2$

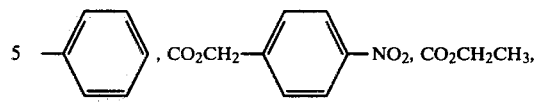

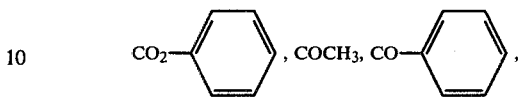

CHO, CN, or $CON(CH_3)_2$;

$R^8$ is hydrogen, $CH_3$ or $OCH_3$; and $R^7$ is $-H$  $-CH_2OH$  $-CH(OH)CH_3$  $-CH(OH)CF_3$  $-CH_2CH_2OH$

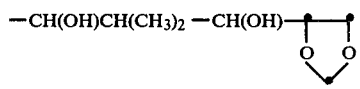

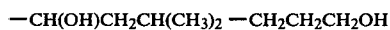

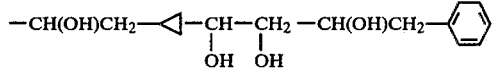

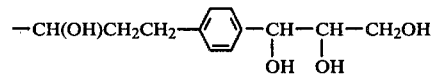

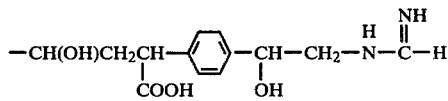

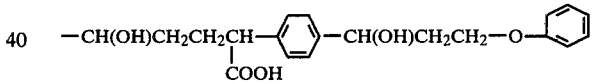

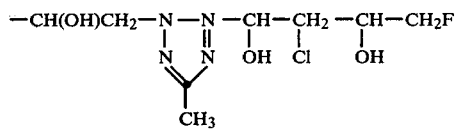

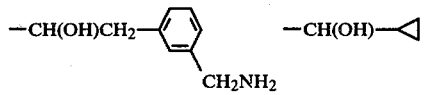

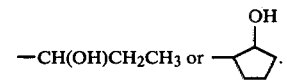

2. The process of claim 1 wherein $R^8$ is hydrogen.
3. The process of claim 2 wherein $R^7$ is

* * * * *